United States Patent [19]

Domb et al.

[11] Patent Number: 5,175,235
[45] Date of Patent: Dec. 29, 1992

[54] BRANCHED POLYANHYDRIDES

[75] Inventors: Abraham J. Domb; Manoj Maniar, both of Baltimore, Md.

[73] Assignee: Nova Pharmaceutical Corporation, Baltimore, Md.

[21] Appl. No.: 532,389

[22] Filed: Jun. 4, 1990

[51] Int. Cl.$^5$ .............................................. C08G 67/04
[52] U.S. Cl. ................... 528/271; 528/220; 525/329.7; 525/451
[58] Field of Search ................ 528/271, 220; 525/329.7, 451

[56] References Cited

U.S. PATENT DOCUMENTS

| | | |
|---|---|---|
| 4,757,128 | 7/1988 | Domb et al. . |
| 4,789,724 | 12/1988 | Domb et al. . |
| 4,792,598 | 12/1988 | Ziegast .................... 528/271 |
| 4,857,311 | 8/1989 | Domb et al. . |
| 4,868,274 | 9/1989 | Gupta et al. ................ 528/271 |
| 4,888,176 | 12/1989 | Langer et al. . |

FOREIGN PATENT DOCUMENTS

| | | | |
|---|---|---|---|
| 0266603 | 5/1988 | European Pat. Off. ........... 528/271 |
| 60-23417 | 2/1985 | Japan .................. 525/451 |
| 60-141725 | 7/1985 | Japan .................. 528/271 |
| 838986 | 6/1960 | United Kingdom ............. 528/271 |
| 869867 | 6/1961 | United Kingdom ............. 528/271 |
| 8901005 | 2/1989 | World Int. Prop. O. ......... 528/271 |

OTHER PUBLICATIONS

Leong, et al., *J. Med. Biomed. Mater. Res.* 19, 941 (1985).
Leong, et al., *J. Med. Biomed. Mater. Res.* 20, 51 (1986).
Rosen, et al., *Biomaterials* 4, 131 (1983).

*Primary Examiner*—Joseph L. Schofer
*Assistant Examiner*—N. Sarofim
*Attorney, Agent, or Firm*—Kilpatrick & Cody

[57] ABSTRACT

Branched polyanhydrides that have superior properties for use in the controlled delivery of substances, prepared by the polymerization of a dicarboxylic acid monomer and a branching agent. The branching agent is a polycarboxylic acid monomer such as 1,3,5-benzenetricarboxylic acid ("BTC"), or an oligomerized fatty acid trimer. Alternatively, the branching agent is a polycarboxylic acid polymer such as poly(acrylic acid) ("PAA"). These branched polymers have significantly higher molecular weights and lower specific viscosity than linear polymers prepared under similar conditions. A major advantage of branched polyanhydrides is that the degradation and release kinetics can be substantially altered without significantly changing the physical properties of the polymer relative to the corresponding linear polymer. By manipulating both the diacid and the branching agent, a wide variety of biodegradable controlled delivery devices for diverse applications can be prepared.

14 Claims, 8 Drawing Sheets

FIGURE 1

POLY (SEBACIC ANHYDRIDE) BRANCHED WITH 1, 3, 5
BENZENETRICARBOXYLIC ACID

POLY (SEBACIC ANHYDRIDE) BRANCHED WITH POLY (ACRYLIC ACID)

* m IS THE NUMBER OF BRANCHING MOLECULES
  ∿ IS A POLYMERIC CHAIN

□ P(SA-ISO-35% Pripol)
+ P(SA-ISO-44% Pripol)

FIGURE 7

□ at 37°C and pH 7.4

BRANCHED POLYANHYDRIDES

This application is a continuation-in-part of U.S. Ser. No. 07/467,635, entitled "Polyanhydrides of Oligomerized Unsaturated Acids," filed on Jan. 19, 1990, by Abraham J. Domb.

BACKGROUND OF THE INVENTION

This invention is in the area of polymers for controlled delivery of substances, and specifically relates to the preparation and use of branched polyanhydrides.

There has been extensive research in the area of biodegradable controlled release systems for bioactive compounds. Biodegradable matrices for drug delivery are useful because they obviate the need to remove the drug-depleted device. The preferred polymeric matrix combines the characteristics of hydrophobicity, stability, strength, flexibility, organic solubility, low melting point, and suitable degradation profile. The polymer must be hydrophobic so that it retains its integrity for a suitable time when placed in an aqueous environment, such as the body, and stable enough to be stored for an extended period before use. The polymer must be strong, yet flexible enough that it does not crumble or fragment during use.

Controlled release devices are typically prepared in one of several ways. The polymer can be melted, mixed with the substance to be delivered, and then solidified by cooling. Melt fabrication requires that the polymer have a melting point that is below the temperature at which the substance to be delivered and polymer degrade or become reactive. Alternatively, the device can be prepared by solvent casting, in which the polymer is dissolved in a solvent, and the substance to be delivered dissolved or dispersed in the solution. The solvent is then evaporated, leaving the substance in the polymeric matrix. Solvent casting requires that the polymer be soluble in organic solvents.

Many polymers have been evaluated for use as the matrix for a delivery device, including polyesters, polyamides, polyurethanes, polyorthoesters, polyacrylonitriles, and polyphosphazenes. None of these polymers have exhibited all of the desired characteristics for use in the controlled delivery of substances.

Polyanhydrides have also been studied for use in controlled delivery devices, as reported by Leong, et al., *J. Med. Biomed. Mater. Res.* 19, 941 (1985); and *J. Med. Biomed. Mater. Res.* 20, 51 (1986). One of the first polyanhydrides studied for its controlled release behavior was poly(bis(p-carboxyphenoxy)methane anhydride), described by Rosen, et al., *Biomaterials* 4, 131 (1983). The aromatic polyanhydride exhibited near zero order (linear) erosion and release kinetics at 37° C. and 60° C. Shortly thereafter, three related polyanhydrides: poly 1,3-(bis(p-carbophenoxy)propane anhydride (p-CPP) (an aromatic polyanhydride); the polymer formed from the copolymerization of p-CPP with sebacic acid (a copolymer of an aromatic diacid and an aliphatic diacid); and polyterephthalic acid (an aromatic anhydride) were prepared and examined for release rates by Leong, et al., *J. Med. Biomed. Mater. Res.* 19, 941 (1985).

The aromatic polyanhydrides were found to have unacceptably slow degradation rates. For example, it was estimated that it would take more than three years for a delivery device prepared from p-CPP to completely degrade in vivo. Further, anhydride homopolymers based on aromatic or linear aliphatic dicarboxylic acids were found to be highly crystalline and have poor film forming properties. Aromatic polyanhydrides also have high melting points and low solubility in organic solvents.

Polymers prepared from linear aliphatic diacids are hydrophilic solids that degrade by bulk erosion, resulting in a rapid release of the drug from the polymeric matrix. Hydrophobicity can be increased by copolymerizing the linear aliphatic diacids with aromatic diacids, however this approach results in an increase in the polymer melting temperature and a decrease in solubility in organic solvents. Furthermore, it does not improve the drug release profile but instead increases the degradation and the elimination time of the polymer both in vivo and in vitro. Since both homopolymers and copolymers of linear aliphatic diacids are very sensitive to moisture, they require extremely anhydrous and low temperature storage conditions.

As described in U.S. Pat. No. 4,757,128 to Domb and Langer, high molecular weight copolymers of aliphatic dicarboxylic acids with aromatic diacids are less crystalline than aromatic or linear aliphatic polyanhydrides, and they form flexible films. Degradation rates are also increased by copolymerizing an aromatic dicarboxylic acid with an aliphatic diacid; however, bulk erosion stll occurs because areas of the polymer containing aliphatic anhydride linkages erode faster than aromatic anhydride linkages, leaving channels in the matrix through which the substance to be delivered is released in an uncontrolled fashion. For example, in the p-CPP sebacic acid copolymer, the aliphatic anhydride bonds are cleaved in vivo and all of the drug released in ten days, while the aromatic regions remain intact for another five and one-half months. Further, the copolymers have inferior mechanical properties; they become brittle and crumble into flakes on exposure to moisture.

U.S. Patents that describe the use of polyanhydrides for controlled delivery of substances include: U.S. Pat. No. 4,857,311 to Domb and Langer, entitled "Polyanhydrides with Improved Hydrolytic Degradation Properties", which describes polyanhydrides with a uniform distribution of aliphatic and aromatic residues in the chain, prepared by polymerizing a dicarboxylic acid with an aromatic end and an aliphatic end); U.S. Pat. No. 4,888,176 to Langer, Domb, Laurencin, and Mathiowitz, entitled "Controlled Drug Delivery High Molecular Weight Polyanhydrides", which describes the preparation of high molecular weight polyanhydrides in combination with bioactive compounds for use in controlled delivery devices); and U.S. Pat. No. 4,789,724 to Domb and Langer, entitled "Preparation of Anhydride Copolymers", which describes the preparation of very pure anhydride copolymers of aromatic and aliphatic diacids.

There is clearly a need for a type of polyanhydride that has a high molecular weight, that also has superior mechanical properties such as flexibility and low specific viscosity. It would also be useful to be able to substantially alter the degradation and release kinetics of the polyanhydide for a wide variety of applications without significantly affecting the physical properties of the polymer.

It is therefore an object of the present invention to provide a biodegradable polymer that releases an incorporated substance in a controlled manner, having a high molecular weight in combination with superior mechanical properties.

It is yet another object of the present invention to provide a polymer with a degradation and release profile that can be substantially altered without significant alteration of the physical properties of the polymer.

SUMMARY OF THE INVENTION

Branched polyanhydrides are provided that have superior properties for use in the controlled delivery of substances in vivo. The branched polyanhydrides are prepared by the polymerization of a dicarboxylic acid monomer and a branching agent. The branching agent is a polycarboxylic acid monomer such as 1,3,5-benzenetricarboxylic acid ("BTC"), or an oligomerized fatty acid trimer, or a polycarboxylic acid polymer such as polyacrylic acid ("PAA"). Branched polyanhydrides have high molecular weights, in the range of 140,000 to 250,000 weight average molecular weight ($M_w$), but are flexible and pliable. The molecular weights of the polymers are substantially higher, and specific viscosity lower, than the corresponding linear polyanhydrides without the branching agents, and are therefore less brittle and have less of a tendency to crumble. Films made from branched polyanhydrides containing fatty acid dimers and trimers degrade into a soft film that gradually disappears without forming harmful sharp flakes. The lower specific viscosity allows for easier melt fabrication of the controlled delivery device.

These polymers degrade over a period of days, and release incorporated substance at a rate corresponding to their degradation rate. The aqueous degradation rates and profiles of branched polyanhydrides, as well as the rates of release of incorporated compound, are manipulated by the selection of the type of dicarboxylic acid and branching agent used to prepare the polymer.

A major advantage of branched polyanhydrides is that the degradation and release kinetics can be substantially altered without significantly changing the physical properties of the polymer relative to the corresponding linear polymer. By manipulating both the diacid and the branching agent, a wide variety of biodegradable controlled delivery devices for diverse applications can be prepared. The solubility can also be manipulated by controlling the polymerization times.

Branched polyanhydrides prepared as described herein are useful in a wide variety of medical applications, including the controlled delivery of bioactive substances and as coatings for implantable devices. The polyanhydrides can also be used for nonmedical applications, including the controlled delivery of insecticides and fungicides.

DETAILED DESCRIPTION OF THE INVENTION

As used here, the term "branched polyanhydride" refers to polyanhydrides prepared by the copolymerization of an aromatic or aliphatic dicarboxylic acid with a polycarboxylic acid monomer or polymer ("branching agent"), wherein the polymerization is stopped before the gel point. The term "crosslinked polyanhydride" as used here refers to branched polyanhydrides that have been allowed to polymerize past the gel point.

Branched polymers are characterized by branch points from which emanate a number of polymer chains in either a random, star like form or a comb-like form. Polyanhydrides prepared with polycarboxylic acid monomeric branching agents are random copolymers with "star point" emanations. Polyanhydrides prepared with polycarboxylic acid polymeric branching agents are graft copolymers with "comb-like" emanations. Long chain branching results in a decrease in specific viscosity relative to the corresponding unbranched polymer of similar molecular weight.

Examples of suitable polycarboxylic acids for use in the preparation of branched polyanhydrides include 1,3,5-benzenetricarboxylic acid ("BTC"), fatty acid trimers, and poly(acrylic acid) ("PAA") and its derivatives.

The molecular weights of the branched polyanhydrides are significantly higher (weight average $M_w$ ranging from approximately 150,000 to 250,000 for poly(sebacic acid) branched with PAA or BTC) than the molecular weight of linear polymers such as poly(sebacic acid anhydride) p(SA) (weight average $M_w$ of 80,000) prepared under the same conditions. Branched polyanhydrides prepared with certain polycarboxylic acid polymers, for example poly(acrylic acid), exhibit a molecular weight that increases linearly with increasing concentration of branching agent.

A substance to be delivered can be incorporated into the matrix of a branched polyanhydride by any appropriate method, including solution fabrication, melt fabrication, and compression molding. The highly crosslinked polyanhydrides that are not soluble in organic solvents can be loaded with the substance to be delivered by swell fabrication. In this method, the substance to be delivered is first dissolved in a solution that the crosslinked polyanhydride is not soluble in. The polyanhydride is then added to the solution, where it swells, drawing the solution into its matrix. The solvent is then removed from the polymer, for example, by evaporation, leaving the substance entrapped in the polyanhydride matrix.

The release of drug from branched polymers is somewhat slower than from the corresponding linear polymers. Longer release times are advantageous in the treatment of certain diseases such as cancer. Drug release from the matrix can be manipulated by the proper selection of the branching agent and the degree of branching in the polymer. For example, the release of morphine from PAA branched polyanhydrides increases with increasing concentration of branching agent. The release rate and total amount of drug released from both PAA and BTC branched sebacic acid polymers approaches that of the corresponding linear polyanhydride p(SA).

A major advantage of branched polyanhydrides is that the degradation and release kinetics can be substantially altered without significantly changing the physical properties of the polymer relative to the corresponding linear polymer. By manipulating both the diacid and the branching agent, a wide variety of biodegradable controlled delivery devices for diverse applications can be prepared. For example, poly(sebacic acid-isophthalic acid) (9:1 by weight) branched with approximately 9% of the oligomerized fatty acid trimer of oleic acid degrades faster and releases incorporated substance faster than the same polymer prepared with 11% of the fatty acid trimer. Poly(sebacic acid) branched with 0.5% of either BTC or PAA is substantially degraded in aqueous buffer after about 20 hours, whereas poly(sebacic acid-isophthalic acid) (9:1 by weight) branched with 5% of the oligomerized fatty acid trimer of oleic acid is only 70% degraded after 90 hours.

Biodegradable biocompatible polyanhydride films prepared from branched or crosslinked polyanhydrides can be used as physical barriers for adhesion prevention (Linsky, C. B., et al., *J. Reprod. Med.* 32, 17 (1987)). They can also be used for controlled release of drugs, including morphine, tetracyline, ibuprofen, marcaine, methotrexate, dexamethazone and triamcinolone. The release devices can be used to provide medication to target organs. Examples are films containing heparin for the prevention of blood clotting, and films releasing dexamethasone or cyclosporin to prevent organ transplant rejection. Branched and crosslinked polyanhydride films also are useful in guided tissue regeneration in periodontal disease (Nyman et al., *J. Clin. Perio.* 9, 290 (1982); ibid 3, 604 (1986); ibid 14, 618 (1987); ibid 15, 288 (1988)) or as tubes for nerve guided regeneration (U.S. Pat. No. 4,870,966 to Dellon L. and Mackinnon S. E.).

Branched and crosslinked polyanhydride films can also be used as coatings for implantable devices, i.e., stents, catheters, artificial vascular grafts, and pacemakers. The coating can release antibiotics, anti-inflammatories, or anti-clotting agents at a predetermined rate, to prevent complications related to the implanted devices. Controlled delivery devices prepared from these polyanhydrides can also be used as ocular inserts for extended release of drugs to the eye.

Branched and crosslinked polyanhydrides are also useful for nonmedical applications, including the controlled release of insecticides and fungicides.

The synthesis of the branched polyanhydrides of the present invention are described in detail as follows:

I. DICARBOXYLIC ACIDS

Any dicarboxylic acid can be copolymerized with the appropriate branching agent to provide a branched or crosslinked polyanhydride. Biocompatible, nontoxic, dicarboxylic acids are preferred for the preparation of polyanhydrides for medical applications.

Nonlimiting examples of suitable dicarboxylic acids include sebacic acid, adipic acid, isophthalic acid, terephthalic acid, fumaric acid, dodecanedicarboxylic acid, azeleic acid, pimelic acid, suberic acid (octanedioic acid), itaconic acid, biphenyl-4,4,-dicarboxylic acid, and benzophenone-4,4,-dicarboxylic acid.

Dicarboxylic acids that can be used in the branched polyanhydride include dicarboxylic acids having an aliphatic end and an aromatic end, for example, p-carboxyphenoxyalkanoic acid.

II. SELECTION OF POLYCARBOXYLIC ACIDS USED IN THE PREPARATION OF BRANCHED POLYANHYDRIDES

Polycarboxylic acids are used to create branch points in the polyanhydride matrix. There are several factors to consider when choosing a polycarboxylic acid for incorporation into a polyanhydride. First, if the polyanhydride is to be used for a pharmaceutical purpose, for example, for controlled delivery of drugs in vivo, all of the components, including the branching agent, must be biocompatible and nontoxic. Second, the branching agent will influence the rate and extent of release of substance from the polymer.

Polycarboxylic Acid Monomers as Branching Agents

Suitable polycarboxylic acid monomers that can be copolymerized with a dicarboxylic acid include 1,3,5-benzenetricarboxylic acid, butane-1,1,4-tricarboxylic acid, tricarballylic acid (propane-1,2,3-tricarboxylic acid), and butane-1,2,3,4-tetracarboxylic acid.

Figure 1:
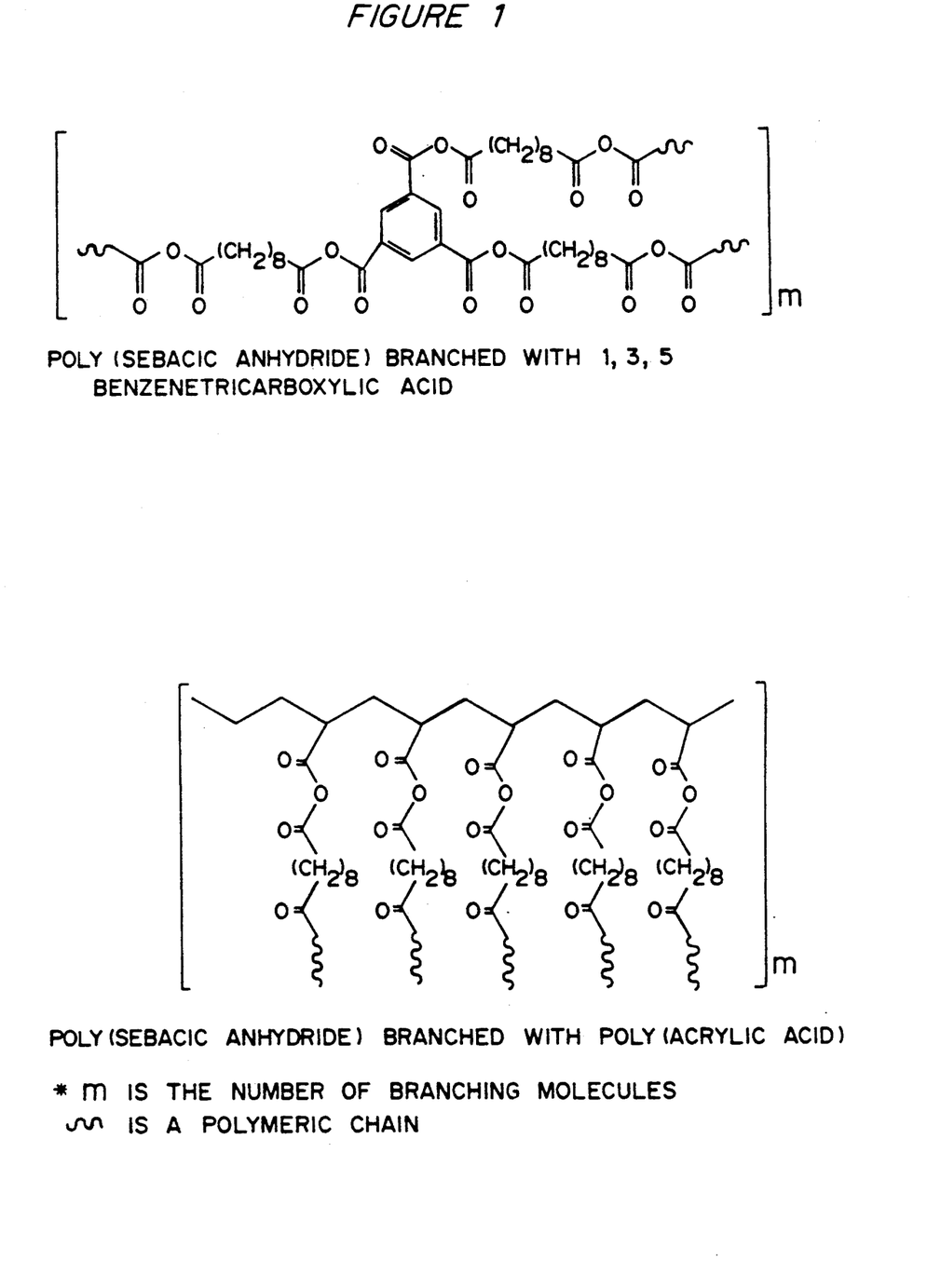
FIG. 1 is an illustration of the chemical structures of poly(sebacic anhydride) branched with 1,3,5-benzenetricarboxylic acid (BTC) and poly(acrylic acid) (PAA).

FIG. 1 is an illustration of the chemical structures of poly(sebacic anhydride) branched with 1,3,5-benzenetricarboxylic acid and with poly(acrylic acid).

As described in copending application U.S. Ser. No. 07/467,635, entitled "Polyanhydrides from Oligomerized Unsaturated Acids," filed on Jan. 19, 1990, by Abraham J. Domb, the trimers of naturally occurring unsaturated fatty acids, such as oleic, erucic, lauroleic, myristoleic, gadoleic, ricinoleic, palmitoleic, linoleic, linolenic, and arachidonic acids, can also be used to prepare polyanhydrides. These fatty acid derivatives should be biocompatible and readily eliminated from the body through the natural digestion mechanism for fatty acids. Oligomerized triacids can be also be synthesized from non-naturally occurring carboxylic acids, such as acrylic, methacrylic, fumaric, crotonic, vinyl acetic (3-butenoic), isocrotonic, allylacetic (4-pentenoic), hexenoic and undecylenic acids. Naturally occurring and synthetic unsaturated acids can also be coupled to form a mixed oligomer for use as a branching agent.

Trimers of oleic acid are very hydrophobic. They add substantial hydrophobicity to polyanhydrides when incorporated into the matrix. As a result, it is not uncommon to find that the more trimer incorporated into the polyanhydride, the longer the release time due to the increased time required to wet the matrix.

Trimers of oleic acid are available from commercial sources. Unichema Chemicals, Inc., Chicago, Ill., sells the trimer as Pripol 1025 (containing 25% by weight of trimer and 75% dimer) and Pripol 1040 (78% trimer and 22% dimer). Henkel Corporation (LaGrange, Ill.) sells Versadyme 213, which is 50-70% of the trimer of oleic acid and 25-40% dimer.

Oligomerized unsaturated carboxylic acid monomers can also be synthesized from the corresponding unsaturated acids by methods known to those skilled in the art.

If the polyanhydride is to be used to deliver other types of substances, including insecticides, fungicides, or pigments, a wide variety of polycarboxylic acids can be used, including those named above and others that are not biocompatible.

Polycarboxylic Acid Polymers as the Branching Agent

Polymers can also be used as branching agents. The choice of polymer will be influenced by whether the resulting branched polyanhydride is to be used for medical applications or nonmedical applications. If the branched polyanhydride is to be used for the in vivo delivery of a bioactive compound, a branching compound should be used that is biocompatible, nontoxic, and that provides a suitable release profile when incorporated into the polymer.

Biocompatible polycarboxylic acid polymers suitable for use in branched polyanhydrides for medical applications include poly(acrylic acid), poly(methacrylic acid) poly(maleic acid) and copolymers thereof.

III. RATIO OF BRANCHING AGENT TO DICARBOXYLIC ACID

Any ratio of dicarboxylic acid to branching agent can be used to prepare the branched polyanhydride, that yields a polyanhydride. The more branching agent that is used, the more flexible and pliable the resulting polymer. An increase or decrease in branching agent will also affect the degradation and release kinetics of the polymer.

As discussed above, the addition of a small amount of branching agent significantly increases the molecular weight of an otherwise linear polymer. However, if too much branching agent is used, the gel point will be reached before there has been sufficient time for polymerization. The result is a polymer mesh of low molecular weight and inferior physical characteristics. The exact amount of branching agent that maximizes molecular weight under given reaction conditions and in combination with a selected dicarboxylic acid must be determined empirically by using methods such as those described in the examples below.

In general, from 0.1 to 15% of branching agent is included in the polyanhydride. For example, it is preferred to use between 0.1% and 2% BTC or PAA branching agent in combination with sebacic acid in the preparation of polymeric matrices for the controlled delivery in vivo of bioactive substances.

IV. POLYMERIZATION OF BRANCHED POLYANHYDRIDES

Branched polyanhydrides can be prepared by methods known to those skilled in the art, including melt polycondensation and solution polymerization of the selected dicarboxylic acid with the desired amount of branching agent.

In the method of melt polycondensation, described by Domb, et al., in *J. Poly. Sci* 25, 3373 (1987), a prepolymer is prepared by heating the diacid and branching agent separately with acetic anhydride to form the corresponding diacetyldianhydride ("diacid prepolymer") and polyacetylanhydride ("branching agent prepolymer"). These prepolymers are then mixed and heated neat under vacuum to form a branched polyanhydride. Acetic acid is stripped off during the polymerization process. Combinations of diacetyldianhydrides and combinations of branching agent prepolymers can also be polymerized with this method.

Solution polymerization is preferred when either the branching agent or the dicarboxylic acid is sensitive to heat. Solution polymerization is described in U.S. Pat. No. 4,916,204 to Domb et al., entitled "One Step Polymerization of Polyanhydrides." Solution polymerization involves the coupling of diacids and branching agent with phosgene in an organic solvent. Poly(4-vinylpyridine-2% divinylbenzene) ("PVP") is added to remove the HCl from solution. For example, diphosgene (0.50 equivalents) is added dropwise to a stirred mixture of diacid (1.0 equivalents) and 1,3,5-benzenetricarboxylic acid (0.03 equivalents) and poly(4-vinylpyridine-2% divinylbenzene) (2.7 equivalents) in 20 ml of chloroform. The solution is stirred for 3 hours at 25° C. The insoluble PVP·HCl is removed by filtration. The solvent is then removed and the precipitate is isolated, washed with ethyl ether, and then dried at 25° C. for 24 hours in a vacuum oven.

The method of preparation and properties of branched polyanhydrides are illustrated in more detail in the following nonlimiting examples. For ease of illustration and comparison among polymers, sebacic acid is used as the dicarboxylic acid, 1,3,5-benzenetricarboxylic acid and fatty acid trimer (Pripol 1025) are used as the tricarboxylic acid monomeric branching agents, and poly(acrylic acid) is used as the polymeric branching agent. However, as stated above, branched polyanhydrides can be prepared from a large variety of dicarboxylic acids and branching agents, under a wide variety of reaction conditions.

Sebacic acid, 1,3,5-benzenetricarboxylic acid, and poly(acrylic acid) (MW 2,000) were purchased from Aldrich Chemical Company (Milwaukee, Wis.). Thermal properties of the polymers were determined with a differential scanning calorimeter (DSC 7, Perkin Elmer, Conn.) using a heating rate of 10° C./min. The molecular weights of the polymers were estimated with a Waters gel permeation chromatography instrument (Waters, Mass.), consisting of a Waters 510 pump and Waters programmable multi-wavelength detector at 254 nm. Samples were eluted in dichloromethane through a Linear Styrogel column (Waters, Mass.) at a flow rate of 1.0 ml/min. Molecular weights of polymers were determined relative to polystyrene standards (Polysciences, Pa., molecular weight range, 400 to 1,500,000) using Maxima 840 computer programs (Waters, Mass.). The viscosities of the polymers were measured in a 1% solution in dichloromethane on a Cannon 50 Ubbelouhde viscometer (Cannon, Pa.) at 25° C. Morphine was analyzed according to the USP method using a Shimadzu C-R4A HPLC system (Shimadzu, Md.) equipped with a C18 column (VWR Scientific, Md.).

EXAMPLE 1

Preparation of Poly(sebacic acid) Branched with 1,3,5-Benzenetricarboxylic Acid and Poly(acrylic acid)

The acetic acid mixed anhydride prepolymers of sebacic acid and the branching agents were prepared by separate reflux of sebacic acid and the branching agents in acetic anhydride for 30 minutes. The isolated prepolymers of BTC and PAA were clear semi-solids. The prepolymer of sebacic acid was then melt polymerized separately with 1,3,5-benzenetricarboxylic acid (BTC) and poly(acrylic acid) (PAA) to yield random and graft type branched polyanhydrides, respectively. Both branching agents were mixed with the diacid in the ratios of 0.5%, 1.0%, 1.5%, and 2.0% by weight to provide a series of branched polymers. Linear polysebacic acid (p(SA)) was also prepared as a reference polymer. The melt polymerization was carried out at 180° C. under a vacuum of 0.1 mm Hg. The reaction was terminated when the polymerization reached the gel point.

The progress of polymerization was monitored by withdrawing samples as a function of time. Each sample was characterized by infrared spectroscopy, gel permeation chromatography, differential scanning calorimetry, and determination of specific viscosity. The chemical structures of the products of these reactions are illustrated in FIG. 1.

Table 1 provides the thermal properties and molecular weights of the synthesized polyanhydrides. As shown, all of the branched polyanhydrides have significantly higher molecular weights (in the range of 144,300 to 263,700 weight average molecular weights) than the reference linear polyanhydride, p(SA) ($M_w$ 81,500). The branched polyanhydrides melt at temperatures between 76° and 80° C. Low melting points are very desirable for melt fabrication of controlled delivery devices. The heat capacity of the polymers is in the range of 74-118 J/gm, suggesting no major differences in the crystallinity of the branched polyanhydrides and the reference linear polyanhydride, p(SA). All of these polyanhydrides are highly soluble in methylene chloride and chloroform, and have similar infrared spectra. The specific viscosities of the branched polyanhydrides are lower than the linear polyanhydrides with similar molecular weight.

TABLE 1

Thermal Properties and Molecular Weight of Branched Polyanhydride[a]

| Polymer | $T_{max}$ °C. | Molecular $M_n$ | Weight $M_w$[b] | Specific Viscosity[c] | Gel Point (min) |
|---|---|---|---|---|---|
| p(SA) | 79 | 12270 | 81521 | 0.742 | — |
| p(BTC-0.5%) | 78 | 40502 | 216598 | 1.031 | 65 |
| P(PTC-1.0%) | 78 | 36830 | 151922 | 0.938 | 45 |
| P(BTC-1.5%) | 80 | 32309 | 144307 | 0.806 | 40 |
| P(BTC-2.0%) | 76 | 32568 | 263713 | 0.798 | 45 |
| P(PAA-0.5%) | 78 | 30606 | 151071 | 0.572 | 80 |
| P(PAA-1.0%) | 79 | 31873 | 188342 | 0.790 | 75 |
| P(PAA-1.5%) | 79 | 31782 | 203521 | 0.742 | 60 |
| P(PAA-2.0%) | 76 | 30513 | 246828 | 0.868 | 60 |

[a]polymerized at 180° C. and under vacuum of 0.1 mm Hg.
[b]Molecular Weight was determined by gel permeation chromatography just before the gel point.
[c]Specific viscosity was measured at 25° C. in a 1% w/v solution in dichloromethane.

EXAMPLE 2

Figure 2:
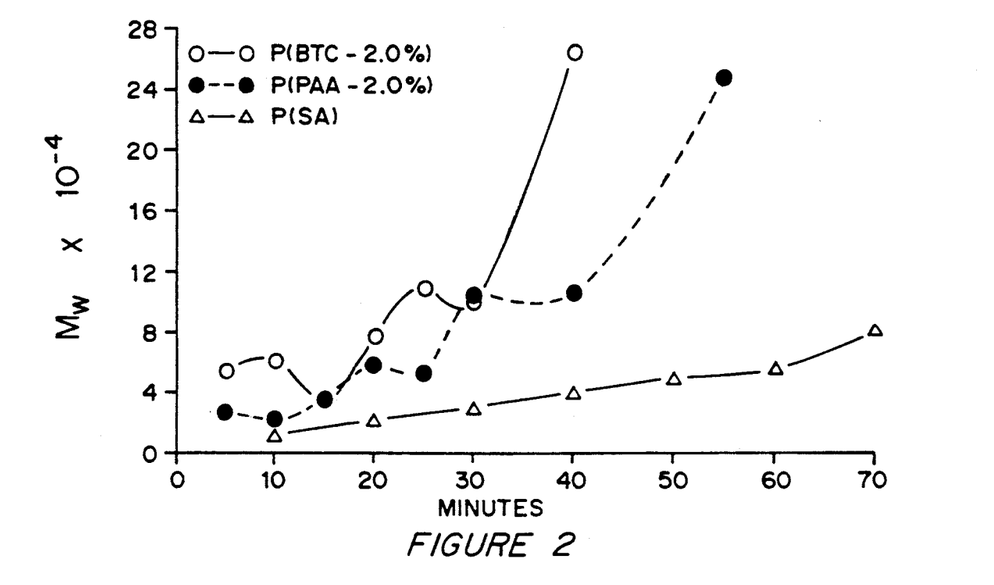
FIG. 2 is a graph of the weight average molecular weight ($\times 10^{-4}$) versus time of polymerization in minutes for poly(sebacic acid) (p(SA)), poly(sebacic acid) polymerized with 2% by weight of poly(acrylic acid) (P(PAA-2.0%)), and poly(sebacic acid) polymerized with 2.0% by weight to 1,3,5-benzenetricarboxylic acid (P(BTC-2.0%)).

Characterization of Branched Polyanhydrides as a Function of Time of Polymerization FIG. 2 is a graph of the molecular weight ($\times 10^{-4}$) versus time of polymerization in minutes for poly(sebacic acid) (p(SA)), poly(sebacic acid) polymerized with 2% by weight of poly(acrylic acid) (P(PAA-2.0%), and poly(sebacic acid) polymerized with 2.0% 1,3,5-benzenetricarboxylic acid (P(BTC-2.0%). As shown in FIG. 2, the molecular weight of the branched polyanhydrides increases during the course of reaction. The rate of increase can be analyzed by dividing the plot into three phases of reaction. The first phase includes the initial five to ten minutes of polymerization. During this time, there is a rapid increase in the molecular weight (to approximately 40,000) as expected with the melt polycondensation reaction. In the second phase of reaction, during the next 15 to 20 minutes, molecular weight increases very gradually, indicating the formation of moderately sized oligomers. In the last phase of the reaction, the time period before the final gel point is reached, there is a sudden increase of molecular weight. This probably represents the reaction between moderately sized segments, following the complete exhaustion of sebacic acid prepolymer. In the third phase, a very high molecular weight is attained. Further polymerization results in the formation of a gel that is insoluble in common organic solvents. This is probably a result of extensive branching, producing a highly cross-linked material. It is evident that there is a strong influence of branching agent on the time necessary to reach a gel point and on the maximum molecular weight.

The polymerization of poly(sebacic acid) was stopped after 90 minutes since continuing the reaction causes a decrease in molecular weight.

EXAMPLE 3

Effect of Concentration of Branching Agent on Polyanhydride

Figure 3:
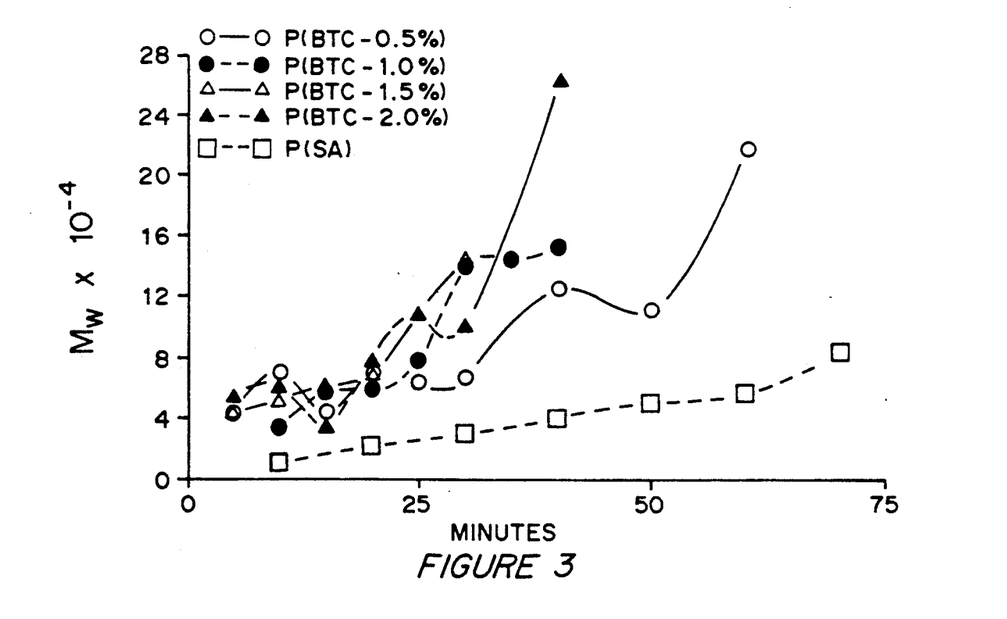
FIG. 3 is a graph of the weight average molecular weight ($\times 10^{-4}$) versus time of polymerization for poly(sebacic acid) polymerized with 0.5%, 1.0%, 1.5%, and 2.0% 1,3,5-benzenetricarboxylic acid.
Figure 4:
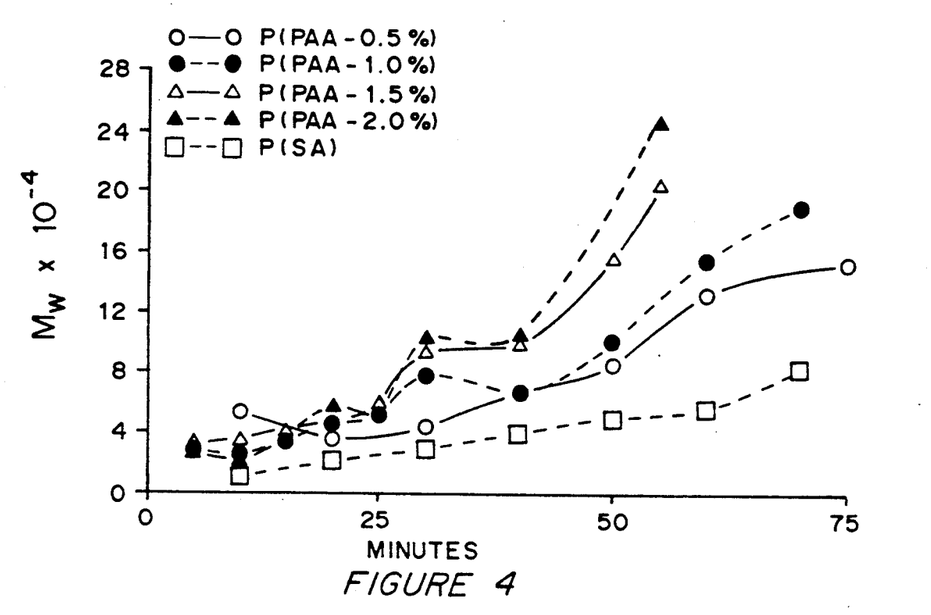
FIG. 4 is a graph of the weight average molecular weight ($\times 10^{-4}$) versus time of polymerization for poly(sebacic acid) polymerized with 0.5%, 1.0%, 1.5%, and 2.0% poly(acrylic acid).

FIG. 3 is a graph of the molecular weight ($\times 10^{-4}$) versus time of polymerization for poly(sebacic acid) polymerized with 0.5%, 1.0%, 1.5%, and 2.0% 1,3,5-benzenetricarboxylic acid. FIG. 4 is a graph of the molecular weight ($\times 10^{-4}$) versus time of polymerization for poly(sebacic acid) polymerized with 0.5%, 1.0%, 1.5%, and 2.0% poly(acrylic acid).

As the concentration of BTC increases, the time required to reach the gel point decreases. At every stage of the reaction, the BTC branched polymers have higher molecular weights than the corresponding linear polymer.

A comparison of FIGS. 3 and 4 indicates that the gel time for polyanhydrides branched with poly(acrylic acid) is relatively longer, and the molecular weight lower, than that for polyanhydrides branched with a similar concentration of BTC at a given point of reaction. Further, BTC branched polyanhydrides have higher molecular weights than PAA branched polyanhydrides of similar concentrations of branching agents. The molecular weights of p(SA) branched with as little as 0.5% of either BTC or PAA branching agent, however, are much higher than that of linear p(SA).

Figure 5:
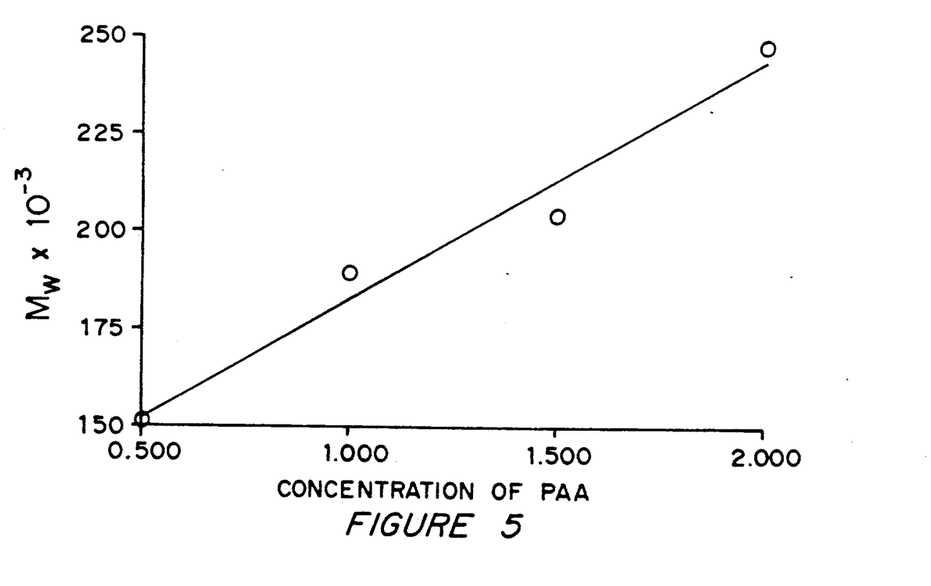
FIG. 5 is a graph of the weight average molecular weight of poly(sebacic acid) branched with poly(acrylic acid) as a function of the concentration of poly(acrylic acid), taken at fifty-five minutes after initiation of polymerization.

The molecular weight of the branched polyanhydrides depends on the concentration of the branching agent. FIG. 5 is a graph of molecular weight of P(SA) samples, taken at fifty-five minutes after polymerization initiation, as a function of the concentration of PAA branching agent. The molecular weight increases linearly ($r^2 > 0.98$) as a function of the concentration of poly(acrylic acid).

EXAMPLE 4

Synthesis of Branched Polyanhydrides using Fatty Acid Trimer

Branched polyanhydrides were synthesized by melt polymerization of prepolymers of sebacic acid and isophthalic acid with various ratios of fatty acid trimer prepolymer (Pripol 1025, Unichema International). Pripol 1025 contains 25% trimer and 75% dimer fatty acid. Therefore, ¼ of the amount of Pripol 1025 used acts as branching agent. The fatty acid dimer that is also in the product is likewise incorporated into the polymer.

The prepolymer of sebacic acid was prepared as described above. The isophthalic acid prepolymer was prepared by refluxing 50 grams of isophthalic acid in 500 ml of acetic anhydride for 10 minutes. The solution was then filtered through a sintered glass funnel and the unreacted acetic anhydride removed under vacuum.

The filtered solution solidified at room temperature. This prepolymer was then further purified by filtration and then recrystallized in 30 ml of toluene and hexane (2:1). The recrystallized pre-polymer was washed with 200 ml of hexane and ether (9:1) to remove the traces of toluene.

For the polymerization reaction, the ratio of sebacic acid prepolymer to isophthalic acid prepolymer was kept constant at 9:1 by weight. The amount of Pripol 1025 varied from 0 to 44% by weight. The appropriate amounts of the prepolymers of sebacic acid, isophthalic acid and Pripol were mixed in a side arm glass test tube. After thorough mixing, the glass test tube was immersed in an oil bath that had been equilibrated at 180° C. After the solids melted, a vacuum of 0.1 mm of Hg was applied to strip off acetic acid. The reaction was carried out for not more than 90 minutes. The resulting polyanhydrides were characterized by specific viscosity, differential scanning calorimetry, NMR, infrared spectroscopy, and gel permeation chromatography. The results are provided in Table 2.

TABLE 2

Thermal Properties and Molecular Weight of Branched polymer P(SA-ISO-Pripol 1025)[a]

| | $T_{max}$ °C. | Molecular Weight $M_u$ | Other Physical Parameter |
|---|---|---|---|
| P(SA-ISO) | 73.8 | 130,000 | — |
| P(SA-ISO-4.5% Pripol) | 71.95 | — | 0.35[c] |
| P(SA-ISO-9% Pripol) | 70.75 | — | 0.80[c] |
| P(SA-ISO-27% Pripol) | 61.41 | Gel | 1850[c] |
| P(SA-ISO-35% Pripol) | — | Gel | 2000[d] |
| P(SA-ISO-44% Pripol) | — | Gel | — |

[a]Polymerized at 180° C. and under vacuum of 0.1 mm Hg for 90 minutes.
[b]Ratio of pre-polymers of SA-ISO is 9:1.
[c]Specific Viscosity measured at 25° C. of a 1% w/v solution in dichloromethane.
[d]Swelling constant determined in dichloromethane, representing percent weight increase.

III. DEGRADATION AND DRUG RELEASE BEHAVIOR OF BRANCHED POLYANHYDRIDES

The degradation and release studies were conducted at 37° C. in 0.1M phosphate buffer, pH 7.4. The buffer was changed at every sampling point.

Degradation and release studies of p(SA) branched with BTC and PAA were conducted on samples loaded with 10% w/w of morphine. Degradation and release studies of p(SA) branched with fatty acid trimer were carried out on samples loaded with methotrexate, tetracycline, marcaine and ibuprofen. Unless otherwise stated, the polymers were melt mixed and cast into a rectangular mold. The slabs were cut into 1×1×0.2 mm, each weighing about 100 mg.

EXAMPLE 5

Aqueous Degradation of Polyanhydrides Branched with Pripol

Figure 6:
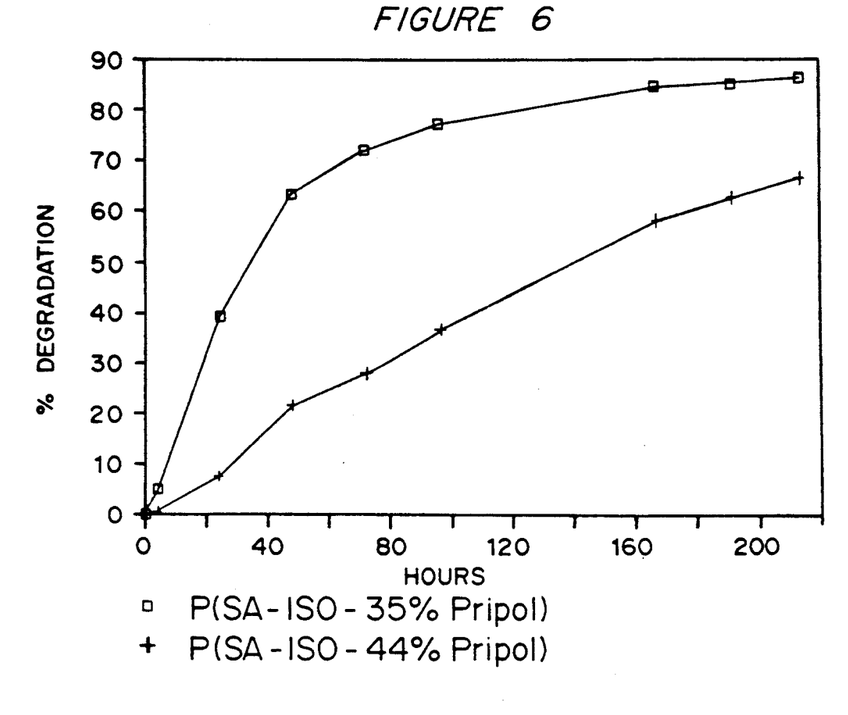
FIG. 6 is a graph of the percent degradation of poly(sebacic acid-isophthalic acid-Pripol 1025) (65% SA-ISO in a weight ratio of 9:1 and 35% Pripol) and poly(sebacic acid-isophthalic acid-Pripol 1025) (56% SA-ISO in a weight ratio of 9:1 and 44% Pripol) over time at 37° C. and in 0.1M phosphate buffer, pH 7.4.

FIG. 6 is a graph of the percent degradation over time of poly(sebacic acid-isophthalic acid-Pripol 1025) (95% SA-ISO in a weight ratio of 9:1 and 5% Pripol) at 37° C. in 0.1M phosphate buffer, pH 7.4. As illustrated, the polyanhydride is approximately 50% degraded in less than 45 hours. The degradation is approximately linear for almost 100 hours.

Figure 7:
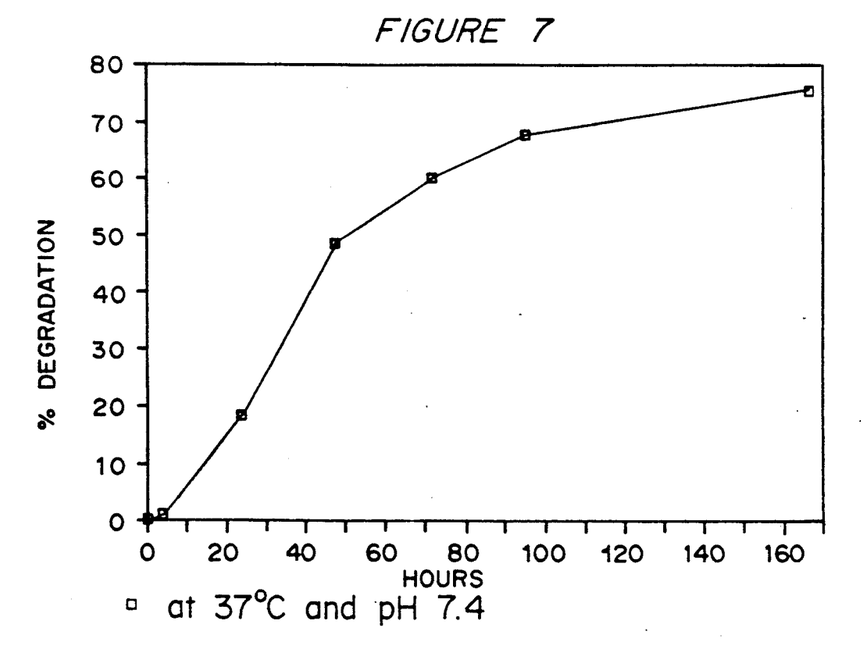
FIG. 7 is a graph of the percent degradation of poly(sebacic acid-isophthalic acid-Pripol 1025) (95% SA-ISO in a weight ratio of 9:1 and 5% Pripol) over time at 37° C. in 0.1M phosphate buffer, pH 7.4.

FIG. 7 is a graph of the percent degradation over time of poly(sebacic acid-isophthalic acid-Pripol 1025) (65% SA-ISO in a weight ratio of 9:1 and 35% Pripol) and poly(sebacic acid-isophthalic acid-Pripol 1025) (56% SA-ISO in a weight ratio of 9:1 and 44% Pripol) at 37° C. in 0.1M phosphate buffer, pH 7.4. As illustrated, poly(SA-ISO) with more pripol branching agent (44% by weight) degrades more slowly than that with less branching agent (35% by weight). The degradation profile of poly(sebacic acid-isophthalic acid-Pripol 1025) (56% SA-ISO in a weight ratio of 9:1 and 44% Pripol) is highly linear for up to 200 hours. The degradation profile of poly(sebacic acid-isophthalic acid-Pripol 1025) (56% SA-ISO in a weight ratio of 9:1 and 35% Pripol) is approximately linear up to 70% degradation (approximately 80 hours).

EXAMPLE 6

Aqueous Degradation of Poly(Sebacic Acid) Crosslinked with 10% and 20% BTC

Poly(sebacic acid) crosslinked with 10% and 20% BTC was prepared as described above, and the rate of degradation over time monitored at 37° C. in 0.1M phosphate buffer, pH 7.4. Degradation was followed by monitoring the weight of the particles and by following the ultraviolet absorbance of the BTC in the degradation medium. The rate of degradation was found to increase with increasing percentage of BTC. The polymers were completely degraded within 96 hours.

EXAMPLE 7

Release of Morphine from Polyanhydrides Branched with BTC and PAA

Figure 8:
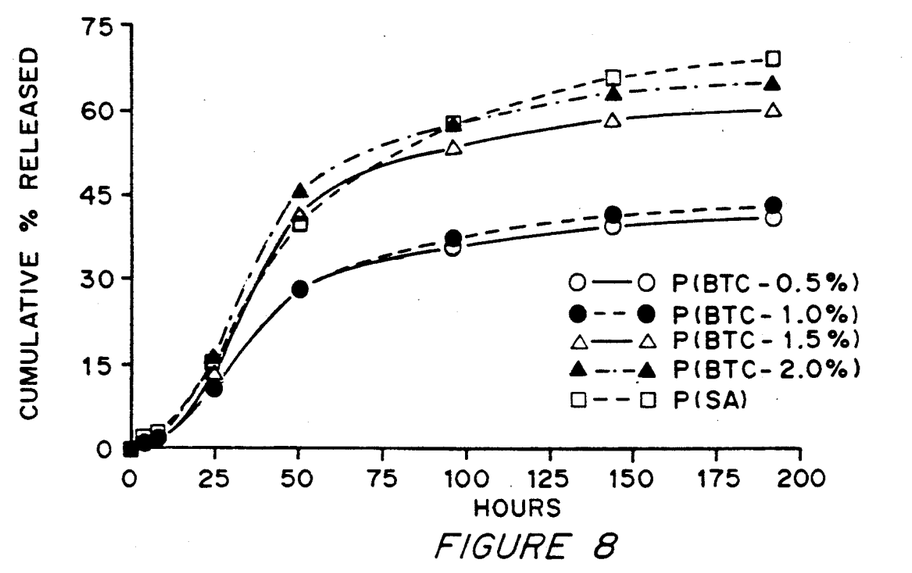
FIG. 8 is a graph of the cumulative percent of morphine released over time by poly(sebacic acid), and by poly(sebacic acid) branched with 0.5%, 1.0%, 1.5%, and 2.0% 1,3,5-benzenetricarboxylic acid, at 37° C. in 0.1M phosphate buffer, pH 7.4.
Figure 9:
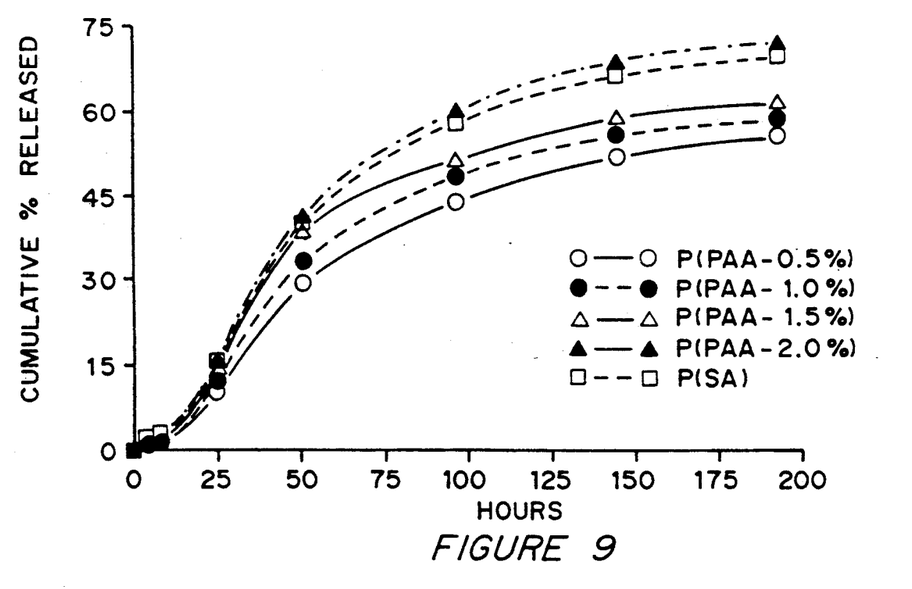
FIG. 9 is a graph of the cumulative percent of morphine released over time by poly(sebacic acid), and by poly(sebacic acid) branched with 0.5%, 1.0%, 1.5%, and 2.0% poly(acrylic acid) at 37° C. in 0.1M phosphate buffer, pH 7.4.

FIG. 8 is a graph of the cumulative percent of morphine released over time from poly(sebacic acid), and from poly(sebacic acid) branched with 0.5%, 1.0%, 1.5%, and 2.0% BTC, at 37° C. in 0.1M phosphate buffer, pH 7.4. FIG. 9 is a graph of the cumulative percent of morphine released over time by poly(sebacic acid), and by poly(sebacic acid) branched with 0.5%, 1.0%, 1.5%, and 2.0% PAA at 37° C. in 0.1M phosphate buffer, pH 7.4.

As shown in FIGS. 8 and 9, as the concentration of BTC and PAA branching agent increases in the polyanhydride, the cumulative percent of drug released increases.

The rate of release of drug from these branched polyanhydrides correlate with the degradation rates of the polymers. A lag time of about eight hours is observed before significant release of drug occurs. As mentioned above, this may be a result of the hydrophobicity of the polymer and the difficulty in wetting the matrix. Once water has penetrated into the matrix, there is a rapid hydrolysis of the anhydride linkages that results in an increased release of drug. After about thirty hours, the release rate gradually decreases until the end of the test. At the end of 196 hours, the test was discontinued because the polymeric matrices fell apart.

On completion of the test, the crumbled matrices were freeze dried and the amount of morphine remaining in the polymer was determined. There was a good correlation between the amount of drug released and the amount left in the polymer, suggesting that the drug is stable in the polymeric matrix.

The release rates and total amount of drug released from PAA branched polyanhydrides (FIG. 9) are higher than that of the corresponding BTC branched polyanhydrides (FIG. 8). The difference between the release of drug from BTC branched polymers and PAA branched polymers is believed to be a result of differences in the structural framework of the polymers.

EXAMPLE 8

Figure 10:
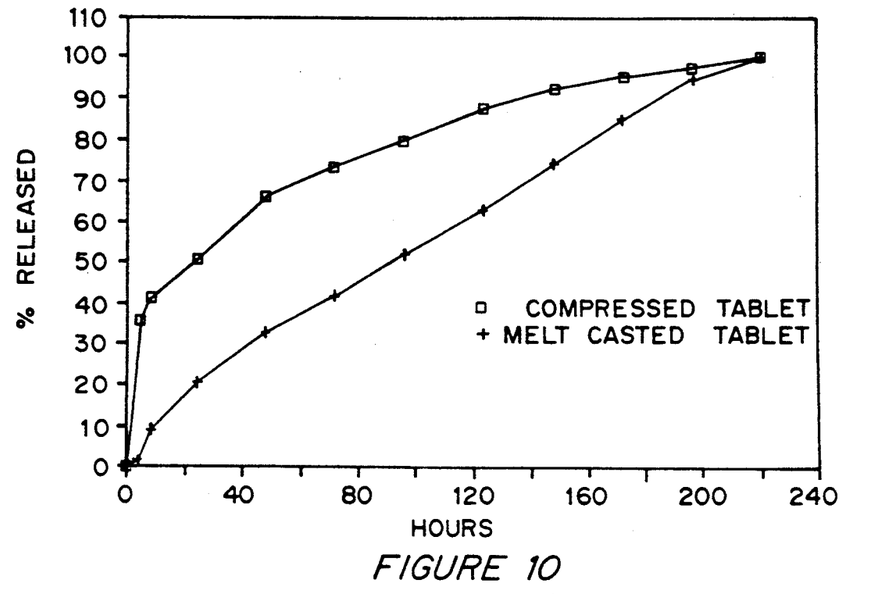
FIG. 10 is a graph of the percent of tetracycline released from compressed and melt cast tablets of poly(sebacic acid-isophthalic acid) (9:1 ratio by weight) branched with 0.5% 1,3,5-benzenetricarboxylic acid over time at 37° C. in 0.1M phosphate buffer, pH 7.4.

Release of Tetracycline from Compressed and Melt Cast Tablets of Polyanhydrides Branched with BTC FIG. 10 is a graph of the percent of tetracycline released from compressed and melt cast tablets of poly(sebacic acid-isophthalic acid) (9:1 ratio by weight) branched with 0.5% BTC. The release studies were conducted at pH 5.0 because tetracycline is not stable at higher pH. At pH 5.0, only 40% of the branched polyanhydride is degraded.

As indicated, the rate and total amount of tetracycline released increases with increasing BTC concentration. The rate and amount of tetracycline released were higher for compression molded tablet than melt cast tablets. The release of drug from compression molded tablets exhibits a burst effect after which the release of drug is fairly linear. Melt cast tablets exhibit an initial lag time followed by linear release for a period of up to 214 hours.

EXAMPLE 9

Release of Methotrexate from Pripol-branched Polyanhydrides

Figure 11:
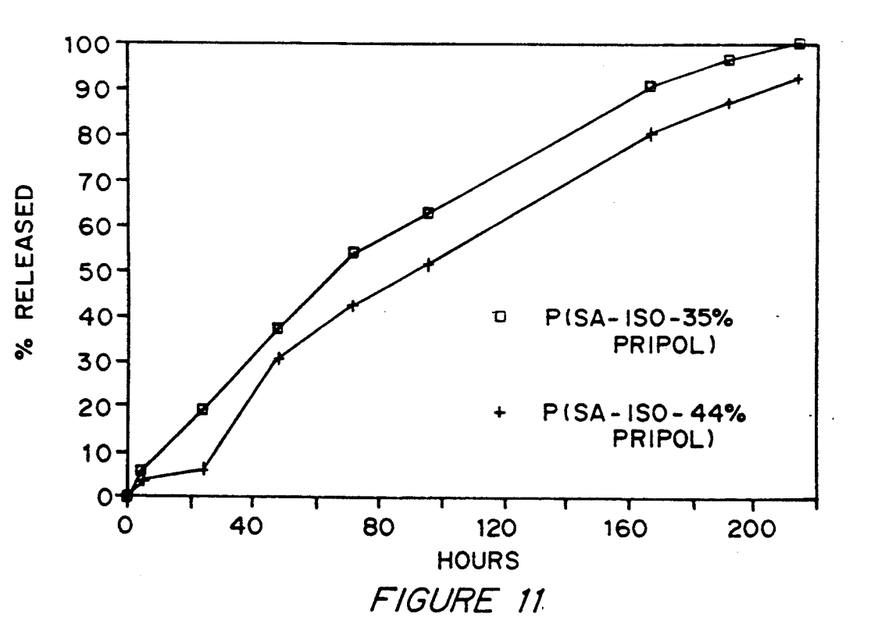
FIG. 11 is a graph of the release of methotrexate from poly(sebacic acid-isophthalic acid-Pripol 1025) (95% SA-ISO in a weight ratio of 9:1 and 35% Pripol) and poly(sebacic acid-isophthalic acid-Pripol 1025) (56% SA-ISO in a weight ratio of 9:1 and 44% Pripol) over time at 37° C. in 0.1M phosphate buffer, pH 7.4.
Figure 12:
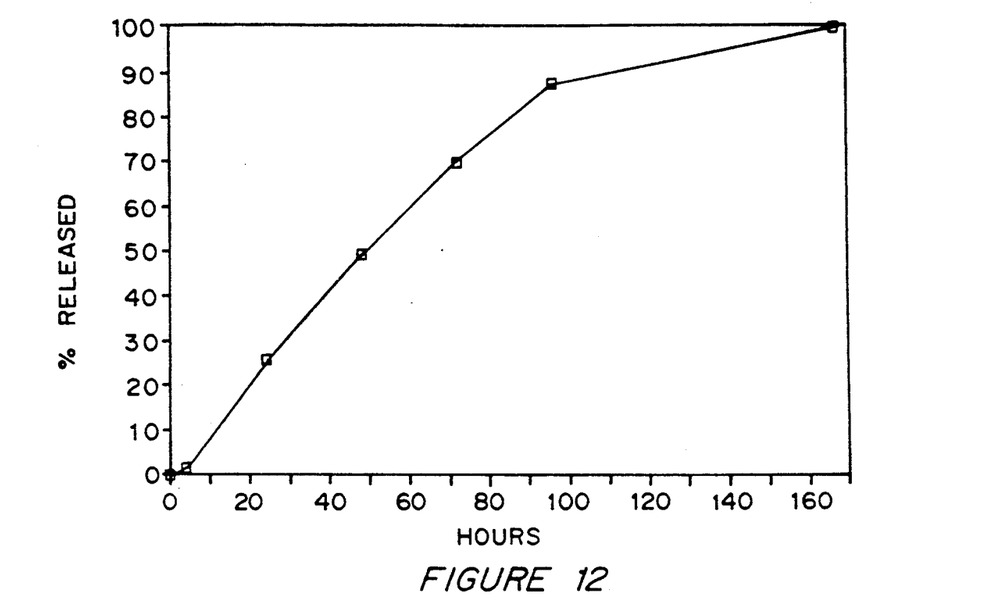
FIG. 12 is a graph of the release of methotrexate over time from poly(sebacic acid-isophthalic acid-Pripol 1025) (95% SA-ISO in a weight ratio of 9:1 and 5% Pripol) at 37° C. in 0.1M phosphate buffer, pH 7.4.

FIG. 11 is a graph of the release of methotrexate over time from melt cast tablets of poly(sebacic acid-isophthalic acid-Pripol 1025) (65% SA-ISO in a weight ratio of 9:1 and 35% Pripol) and poly(sebacic acid-isophthalic acid-Pripol 1025) (56% SA-ISO in a weight ratio of 9:1 and 44% Pripol) at 37° C. in 0.1M phosphate buffer, pH 7.4. FIG. 12 is a graph of the release of methotrexate from poly(sebacic acid-isophthalic acid-Pripol 1025) (95% SA-ISO in a weight ratio of 9:1 and 5% Pripol) over time at 37° C. in 0.1M phosphate buffer, pH 7.4.

The release of drug from all three devices was almost linear. The release of drug increased with decreasing concentration of Pripol. The cumulative amount of drug released varied from 75 to 100% in the first 214 hours. The release of methotrexate correlated with the degradation of the polyanhydride matrices, indicative of surface erosion.

V. INCORPORATION OF DRUG BY SWELLING CROSSLINKED POLYMER IN DRUG LOADED SOLUTION

Substances to be delivered can be incorporated into the matrices of branched polyanhydrides by any suitable method, including the known methods of solution fabrication, melt fabrication, and compression molding.

Branched polyanhydrides that have been polymerized past the gel point to provide crosslinked polymers are not soluble in organic solvents. These crosslinked polyanhydrides are very useful because they can be fabricated "in blank," without substance to be delivered, and then loaded with the substance at a latter date by swell fabrication. Swell fabrication can be used to prepare size restricted drug loaded devices, including microparticles, microspheres, or nanoparticles. The particles of desired size are initially prepared from the crosslinked polyanhydride without drug. The particle is then loaded with drug by the below-described technique, and dried back to its original size. This procedure is especially useful for the incorporation of drugs that are sensitive to mixed solvents, heat, or high shear forces. Branched polyanhydrides that are soluble in organic solvents (not polymerized past the gel point) cannot be fabricated by this method.

In the method of swell fabrication, the substance to be delivered is dissolved in a solvent that the branched polyanhydride is not soluble in, but that causes the polymer to swell. The crosslinked polyanhydride in the form of particles or other matrix of desired shape, is added to the drug solution. The polymer swells, drawing the solution into the matrix. It is preferred to use a minimal amount of solvent so that all of the solution with drug will be absorbed by the polymer. Alternatively, if more solution is used than can be absorbed by the polymer, the polymer is retained in the solution with gentle stirring until the concentration of drug is constant in the unabsorbed soution. The polymer is then removed from the solvent and vacuum dried at a temperature below which the drug and polymer degrade or react. The solvent is removed, leaving the drug in the polymer matrix. The surface layer of the drug is then removed by quickly washing the particles or the device with phosphate buffer.

EXAMPLE 9

Preparation of Delivery Device by Swell Fabrication

Microparticles of poly(sebacic acid) crosslinked with 5% or 10% BTC were placed separately into methylene chloride solutions of marcaine and ibuprofen (0.5 grams in 1 mL solution). The polymers were allowed to swell. After all of the solvent was absorbed the by the polymer particles (about 30 minutes), the solvent was evaporated from the particles using an evaporator. The amount of drug incorporated into the polymer varied from 63% to 81% of the total amount of drug used.

Figure 13:
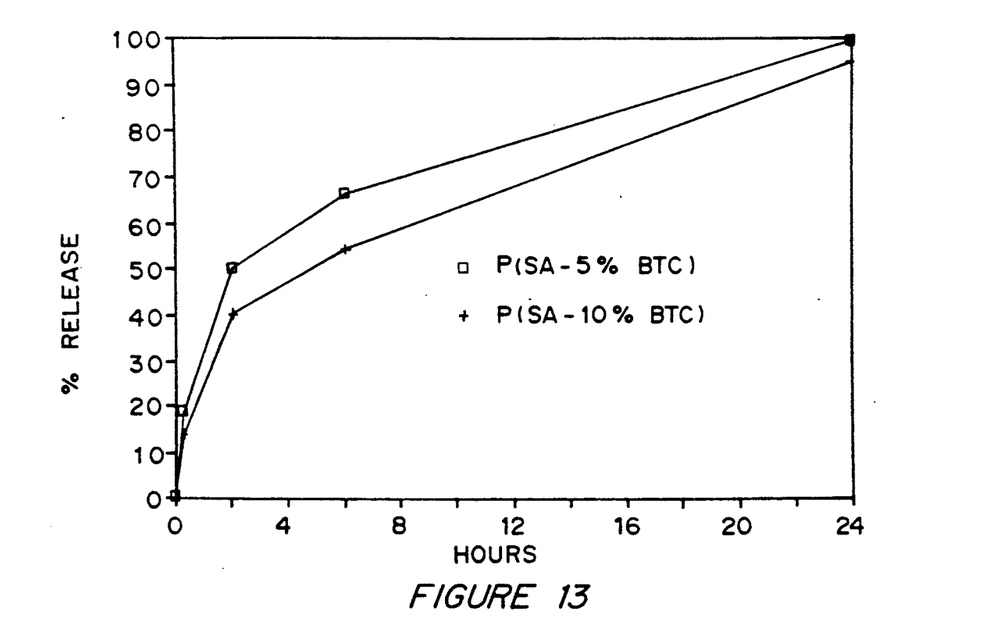
FIG. 13 is a graph of the release of marcaine over time from microparticles of poly(sebacic acid) crosslinked with 5% and 10% 1,3,5-benezenetricarboxylic acid at 37° C. in 0.1M phosphate buffer, pH 7.4.

FIG. 13 is a graph of the release of marcaine over time from crosslinked poly(sebacic acid) branched with 5% and 10% BTC at 37° C. in 0.1M phosphate buffer, pH 7.4. As indicated, the release of drug from the swell fabricated device increases with increasing concentration of BTC.

Figure 14:
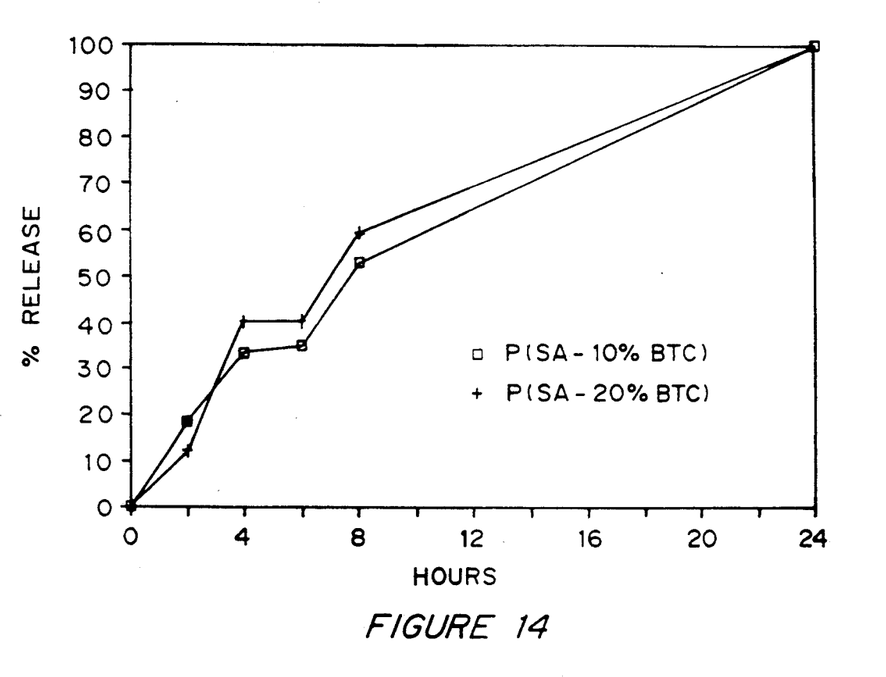
FIG. 14 is a graph of the release of ibuprofen over time from microparticles poly(sebacic acid) crosslinked with 5% and 10% 1,3,5-benzenetricarboxylic acid at 37° C. in 0.1M phosphate buffer, pH 7.4.

FIG. 14 is a graph of the release of ibuprofen from crosslinked poly(sebacic acid) branched with 10% and 20% BTC over time at 37° C. in 0.1M phosphate buffer, pH 7.4. Both devices released drug gradually over a 24 hour period.

Modifications and variations of the present invention, branched and crosslinked polyanhydrides and their method of use, will be obvious to those skilled in the art from the foregoing detailed description. Such modifications and variations are intended to come within the scope of the appended claims.

We claim:

1. A polyanhydride for the controlled delivery of substances prepared by the polymerization of a dicarboxylic acid and a compound selected from the group consisting of a tricarboxylic acid and a polycarboxylic acid branching agent.

2. The polyanhydride of claim 1, wherein the branching agent is a polycarboxylic acid monomer.

3. The polyanhydride of claim 1, wherein the branching agent is a polycarboxylic acid polymer.

4. The polyanhydride of claim 2, wherein the branching agent is selected from the group consisting of 1,3,5-benzenetricarboxylic acid, butane-1,1,4-tricarboxylic acid, tricarballylic acid (propane-1,2,3-tricarboxylic acid), butane-1,2,3,4-tetracarboxylic acid, and oligomerized fatty acid trimers.

5. The polyanhydride of claim 3, wherein the branching agent is selected from the group consisting of poly(acrylic acid), poly($\alpha$-methacrylic acid), poly($\beta$-methacrylic acid), and poly(maleic acid).

6. The polyanhydride of claim 1, wherein the dicarboxylic acid is selected from the group consisting of sebacic acid, adipic acid, isophthalic acid, p-carboxyphenoxyalkanoic acid, terephthalic acid, fumaric acid, dodecanedicarboxylic acid, azeleic acid, pimelic acid, suberic acid (octanedioic acid), itaconic acid, biphenyl-4,4'-dicarboxylic acid, and benzophenone-4,4'-dicarboxylic acid.

7. The polyanhydride of claim 1, wherein mixtures of dicarboxylic acids are polymerized.

8. The polyanhydride of claim 1, wherein mixtures of branching agents are polymerized.

9. The polyanhydride of claim 1, wherein the polymerization is stopped before the gel point.

10. The polyanhydride of claim 1, wherein the polymerization is stopped after the gel point.

11. The polyanhydride of claim 1 of molecular weight greater than 140,000 $M_w$.

12. The polyanhydride of claim 1, wherein the ratio of dicarboxylic acid to branching agent is between 0.1 and 15%.

13. The polyanhydride of claim 1 that is a random copolymer.

14. The polyanhydride of claim 1 that is a graft copolymer.

* * * * *